United States Patent
Pegard et al.

(10) Patent No.: US 12,133,909 B2
(45) Date of Patent: Nov. 5, 2024

(54) USE OF EVODONE OR A DERIVATIVE THEREOF AS A COOLING AGENT

(71) Applicant: ROBERTET S.A., Grasse (FR)

(72) Inventors: Anthony Pegard, Grasse (FR); Sophie Lavoine, Mouans Sartoux (FR); Marina Humbert, Grasse (FR)

(73) Assignee: ROBERTET S.A., Grasse (FR)

( * ) Notice: Subject to any disclaimer, the term of this patent is extended or adjusted under 35 U.S.C. 154(b) by 667 days.

(21) Appl. No.: 17/433,087

(22) PCT Filed: Feb. 21, 2020

(86) PCT No.: PCT/FR2020/050326
§ 371 (c)(1),
(2) Date: Aug. 23, 2021

(87) PCT Pub. No.: WO2020/169935
PCT Pub. Date: Aug. 27, 2020

(65) Prior Publication Data
US 2022/0040077 A1    Feb. 10, 2022

(30) Foreign Application Priority Data

Feb. 22, 2019   (FR) .................................. 19/01805

(51) Int. Cl.
*A61K 8/49*        (2006.01)

(52) U.S. Cl.
CPC ...... *A61K 8/4973* (2013.01); *A61K 2800/244* (2013.01)

(58) Field of Classification Search
None
See application file for complete search history.

(56) References Cited

U.S. PATENT DOCUMENTS

2007/0274928 A1   11/2007   Selifonov
2012/0015054 A1*   1/2012   Humbert ................ A01N 65/36
                                                     424/725

FOREIGN PATENT DOCUMENTS

| WO | 2010/103207 A1 | 9/2010 |
| WO | 2016/097496 A1 | 6/2016 |
| WO | 2017/106279 A1 | 6/2017 |

OTHER PUBLICATIONS

May 12, 2020 Search Report issued in International Patent Application No. PCT/FR2020/050326.
Aug. 10, 2021 International Preliminary Report on Patentability issued in International Patent Application No. PCT/FR2020/050326.

* cited by examiner

*Primary Examiner* — Brian Gulledge
(74) *Attorney, Agent, or Firm* — Oliff PLC

(57) ABSTRACT

Use as a cooling agent of a compound of general formula (I)

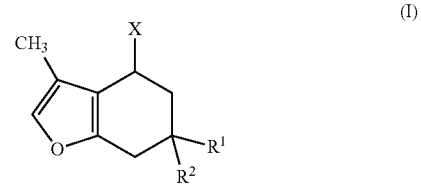

in which:
$R^1$ and $R^2$ are chosen independently of each other as a hydrogen atom or a $C_1$-$C_6$-alkyl group; and
X represents =O, —OAc, —O—$C_1$-$C_6$-alkyl, —N—OH or —OH.

10 Claims, No Drawings

USE OF EVODONE OR A DERIVATIVE THEREOF AS A COOLING AGENT

The present invention relates to the use of evodone or one of its derivatives as a cooling agent.

Throughout the human body, and in particular on the skin or the oral mucosas, different receptors allow perceiving various sensations. Nocireceptors, for example, allow perceiving pain.

Among the nocireceptors, there are free nerve endings in the skin, close to blood capillaries, sensitive to cold or heat: these are thermoreceptors or TRP (Transient Receptor Potential), ion channels that open above or below a temperature threshold which depends on the receiver.

The TRP receptor family comprises more than 30 cation channels and may be divided into seven main subfamilies. TRP channels and TRP-related receptors suggest a sensory response to all thermal exposures, selectively responding to threshold temperatures ranging from harmful heat to harmful cold as well as some chemicals reproducing these sensations.

The heat receptors, related to C-type amyelin fibers, are deeper in the dermis. Heat-sensitive nerve endings of the skin begin to emit action potentials when subjected to a temperature of around 30° C. The more the temperature increases, the more the frequency of the potentials formed increases. Nevertheless, above 45° C., this frequency decreases (as if the stimulus were weaker). Conversely, the nocireceptors, these pain-sensitive fibers, begin to emit action potentials from this temperature.

The cold receptors, related to fine myelin fibers, are superficial, located in the epidermis. Cold-sensitive nerve endings begin to emit action potentials around 35° C. The frequency of these potentials increases when the temperature drops (it reaches its maximum at about 25° C. and then decreases to 10° C.).

There are two genes, TRPM8 and TRPA1, known to be cold sensitive TRP channels. In particular, it is known that TRPM8, also called CMR1 (Cold and Menthol Receptor 1), is stimulated by low temperatures as well as by so-called "coolant" compounds.

"Coolant" compounds allowing obtaining a cold thermal effect are very often used in cosmetics, hygiene or toiletry products, or else in food products, in order to simulate a cooling effect. The use of such compounds or "cooling agents" makes it possible in particular to reinforce the freshness valence, the toning effect or the sensation of hydration, thus making it possible to supplement and/or amplify the effectiveness of the products in which they are incorporated.

Among the most commonly used cooling agents, mention may in particular be made of menthol or else icilin, menthone, eucalyptol, geraniol and linalool. These agents have a stimulating effect on the TRPM8 channel which triggers this sensation of freshness.

The utility of these cooling agents, and in particular of menthol and of its derivatives, is however limited by its multi-modal actions on sensory processes, in particular because of its smell and the severity of its taste. The unpleasant effects of menthol can be easily felt, for example, when ointments containing menthol are brought near the surface of the eyes. Menthol vapors injure the eye and cause tearing.

Thus, at the date of the present invention, it remains necessary to identify new compounds capable of stimulating the TRPM8 channel and therefore of being used as cooling agents in cosmetic products, hygiene or toiletry products, or else in food products, but not having the same disadvantages as menthol in terms of smell or taste.

Evodone, or 6-dimethyl-6,7-dihydro-5H-1-benzofuran-4-one, can be synthesized or isolated from extracts obtained from the aerial portions of the Euodia suaveolens Scheff plant. As indicated by the international patent applications WO-A 2010/103207 and WO-A-2016/097496, evodone and its close derivatives are in particular known for their repellent properties against insects, in particular mosquitoes.

However, the possible effect of evodone or its derivatives on the TRPM8 channel or their use as a cooling agent has never been described at the date of the present invention.

Yet, it has now been found, quite surprisingly, that evodone and its close derivatives stimulate the TRPM8 channel and therefore have cooling properties.

The object of the present invention is therefore the use as a cooling agent of a compound of general formula (I)

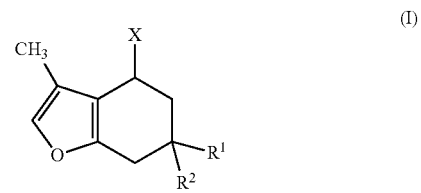

in which:
R$^1$ and R$^2$ are chosen independently of each other as a hydrogen atom or a C$_1$-C$_6$-alkyl group; and
X represents =O, —OAc, —O—C$_1$-C$_6$-alkyl, —N—OH or —OH.

The compounds of formula (I) according to the present invention can be used as cooling agents in cosmetic products, hygiene or toiletry products, or else in food products, with effects comparable to that of menthol or its derivatives, and do not have the same disadvantages as menthol in terms of smell or taste.

In the context of the present invention:
"evodone" refers to 6-dimethyl-6,7-dihydro-5H-1-benzofuran-4-one, the CAS number of which is 529-63-5;
"C$_1$-C$_6$-alkyl" refers to a linear or branched saturated hydrocarbon chain, including from 1 to 6 carbon atoms, in particular the methyl or ethyl group; and
"cooling agent" refers to any compound capable of causing a cold thermal effect when it is applied onto the skin or introduced into the oral cavity, in particular by activating the cold-sensitive TRP channels such as TRPM8 or TRPA1.

An object of the present invention is therefore the use of a compound of formula (I) as defined above as a cooling agent. Preferably, an object of the present invention is the use as a cooling agent of a compound of general formula (I) as defined above in which the following features are chosen alone or in combination:
R$^1$ and R$^2$ are chosen independently of each other as a hydrogen atom or —CH$_3$, —C$_2$H$_5$ or —(CH$_2$)$_2$CH$_3$; more preferably R$^1$ and R$^2$ are identical and are chosen as being a hydrogen atom; and/or
X represents =O, —OAc or —OH; more preferably X represents =O.

Almost preferably, the present invention relates to the use of evodone as a cooling agent.

The compounds of formula (I) described above may be prepared by any method known to the skilled artisan.

The compounds of formula (I) described in the context of the present invention may therefore be used as a cooling agent in cosmetic products, hygiene or toiletry products, or else in food products. To this end, these compounds can be included in a composition which can be formulated in any galenic form suitable for its administration.

Thus, the compositions comprising the cooling agent according to the presentre invention can be formulated in the form of a cream, gel, lotion, foam, serum, milk, oil-in-water or water-in-oil emulsion, solution, unguent, sprayer, aftershave lotion, soap, shampoo, powder, stick pack, pencil and stick for makeup, foundation, drink, candy and chewing gum.

These compositions contain the cooling agent according to the present invention in a ratio of from 0.005% to 75% by total weight of the composition, preferably from 0.01% to 25%, more preferably from 0.1% to 5%.

For preparing of these compositions, the cooling agent used in the context of the present invention is mixed with the excipients conventionally used in cosmetics or nutraceuticals.

The compositions comprising the extract used in the context of the present invention may be in the form of a cream in which the cooling agent used in the context of the present invention is combined with the excipients commonly used in cosmetology.

These compositions may also be in the form of gels in the appropriate excipients such as cellulose esters or other gelling agents, such as carbopol, sepinov (polyacrylate), guar gum, etc.

These compositions may also be in the form of a lotion or a solution in which the cooling agent used in the context of the present invention is in an encapsulated form. The microspheres may consist for example of fatty substances, agar and water. The cooling agent used in the context of the present invention can be incorporated into vectors such as liposomes, glycospheres, cyclodextrins, in chylomicrons, macro-, micro-, nano-particles as well as macro-, micro- and nanocapsules, and also can be absorbed on powdery organic polymers, talcs, bentonites and other mineral carriers.

These emulsions have good stability and can be preserved for the time necessary for use at temperatures comprised between 0 and 50° C. without any sedimentation of the constituents or separation of the phases.

The compositions comprising the cooling agent used in the context of the present invention may also contain additives or adjuvants customary in cosmetology, such as, for example, antimicrobial agents or perfumes, but also extraction or synthetic lipids, gelling polymers and viscosifiers, surfactants and emulsifiers, water-soluble or liposoluble active ingredients, plant extracts, tissue extracts, marine extracts, synthetic active ingredients.

The compositions comprising the cooling agent used in the context of the present invention may also comprise other cooling active ingredients such as citriodiol or cubeb pepper and/or complementary active ingredients chosen for their action, for example for their nutritional effect, slimming effect, anti-cellulite effect, firming effect, moisturizing effect, anti-aging effect, antimicrobial activity, anti-oxidant activity, antiradical activity, healing effect, tightening effect, anti-wrinkle effect, chelating activity, complexing and sequestering activity, soothing effect, anti-dark circles effect, anti-redness effect, emollient activity, hair detangling effect, anti-dandruff activity, hair regrowth stimulating effect, hair loss inhibiting effect, capillary sheathing effect, depilatory activity, activity limiting hair regrowth, activity participating in cell renewal, activity modulating the inflammatory response, the activity participating in maintaining facial contours, and also sun protection, anti-irritant activity, cellular nutrition, cellular respiration, anti-seborrheic treatments, skin tone, hair protection.

When the compositions comprising the cooling agent used in the context of the present invention contain additional active ingredients, these are generally present in the composition at a sufficiently high concentration so they could carry out their activity.

The compositions comprising the cooling agent used in the context of the present invention are very well tolerated, they exhibit no toxicity and their application onto the skin or their introduction into the oral cavity, even for prolonged periods of time, would not imply any systematic effect.

The present invention is illustrated in a non-limiting manner by the following examples.

EXAMPLE 1

Cream Containing Evodone

Creams (water-in-oil emulsion) containing respectively:
1% of evodone—cream 1;
1% of Frescolat ML (i.e. menthyl lactate)—cream 2;
1% of Eucalydiol (i.e. citriodiol)—cream 3;
1% of $CO_2$ extract of cucebe (30% cubelol)—cream 4;
are prepared.

To measure the cooling effect, 100 mg of one of the creams 1 to 4 or of a placebo are applied onto the inner side of both forearms of persons who have agreed to test the product. After one minute, each participant is asked to rate the cooling effect on a scale of 0 to 3 (i.e. score), with 3 being the maximum effect.

Each cream (including the placebo) is applied randomly and blindly to the forearms of 17 people.

The obtained results are reported in Table 1 below.

TABLE 1

| Cooling power of the creams 1 to 4 | |
|---|---|
| Tested cream | Cooling power (obtained by adding the scores) |
| Cream 1 | 30 |
| Cream 2 | 25 |
| Cream 3 | 15 ($p < 0.05$) |
| Cream 4 | 30 |

It should be noted that evodone has a cooling effect similar to that which can be provided by molecules such as citriodiol or cubebol found in the CO2 extract of cubebe pepper. In addition, the cooling effect is significantly greater than that obtained with menthyl lactate (i.e. Frescolat ML—commercial reference).

EXAMPLE 2

Cream Containinci Evodone 2.1—Experimental Protocol

For this study, the cooling effect of 5 compositions containing different cooling agents is evaluated in vivo according to the following protocol.

22 female subjects aged from 18 to 63 were selected. On the back of each subject, between the two scapulas, six areas of 3 cm×2.5 cm are delimited. On 5 areas chosen each time randomly, 15 mg of the compositions to be tested are applied. Nothing is applied onto the sixth area (i.e. control).

From the time of application of the creams (T0), the skin temperature of the different zones is measured on each subject using a thermal camera (Thermovision SC6000HS (Flirsystems)—resolution 640×512—frequency 125 Hz) at the following times: T0, T0+15 s, T0+30 s, T0+45 s, T0+1 min, T0+1 min30 s, T0+2 min, T0+3 min, T0+4 min, T0+5 min, T0+6 min, T0+8 min and T0+10 min. The measurements are performed at 21° C.±1.5° C., the subject lying on his stomach and motionless. The temperatures are measured with an accuracy of around 0.10° C.

A variance test (ANOVA) is used to compile and validate the results. The normality of the ANOVA residues is verified by the Shapiro-Wilk test with a significance level set at 1%, and the homogeneity of the variances on the residues is verified by a Levene test at 5%.

If these two conditions are met, the statistical analysis allowing comparing the parameters measured at the different times is conducted by a one-factor variance analysis (ANOVA) test on repeated measurements. The significance level is set at 5%.

If one of the two conditions is not met, the statistical analysis is performed by an ANOVA on the data transformed into ranks, at a threshold of 5%.

If there is a significant difference in ANOVA, a 5% Dunnett test is performed to compare all kinetic times to T0.

2.2—Used Compositions

The creams 1 to 4 described in example 1 were tested. In addition, cream 5 containing 33.3% of evodone/33.3% of eucalydiol/33.3% of cubeb extract (30% cubebol) has also been tested.

2.3—Experimental Results

The obtained experimental results are reported in Table 2 below.

TABLE 2

Cooling power of the creams 1 to 5

| Time T | Applied cream | | | | |
|---|---|---|---|---|---|
| | Cream 1 | Cream 2 | Cream 3 | Cream 4 | Cream 5 |
| | Temperature deviation (in ° C.) | | | | |
| T0 | −0.1 | −1.0 | −1.1 | −1.2 | −0.9 | −1.2 |
| T0 + 15 s | −0.1 | −1.1 | −1.3 | −1.2 | −1.0 | −1.2 |
| T0 + 30 s | −0.2 | −1.3 | −1.4 | −1.4 | −1.2 | −1.4 |
| T0 + 45 s | −0.1 | −1.5 | −1.6 | −1.5 | −1.3 | −1.5 |
| T0 + 1 min | −0.2 | −1.6 | −1.7 | −1.6 | −1.4 | −1.6 |
| T0 + 1 min30 s | −0.2 | −1.7 | −1.8 | −1.7 | −1.5 | −1.7 |
| T0 + 2 min | −0.2 | −1.7 | −1.8 | −1.7 | −1.5 | −1.7 |
| T0 + 3 min | −0.2 | −1.4 | −1.6 | −1.5 | −1.3 | −1.5 |
| T0 + 4 min | −0.3 | −1.2 | −1.3 | −1.3 | −1.1 | −1.2 |
| T0 + 5 min | −0.3 | −1.0 | −1.1 | −1.1 | −0.9 | −1.0 |
| T0 + 6 min | −0.3 | −0.9 | −1.0 | −1.0 | −0.8 | −0.9 |
| T0 + 8 min | −0.4 | −0.7 | −0.8 | −0.8 | −0.6 | −0.8 |
| T0 + 10 min | −0.4 | −0.7 | −0.8 | −0.8 | −0.6 | −0.7 |

2.4—Conclusion

It should be noted that evodone has a cooling effect similar to that which can be provided by molecules such as menthyl lactate (i.e. Frescolat ML—commercial reference), citriodiol or cubebol found in the $CO_2$ extract of cubebe pepper.

The invention claimed is:

1. A method for causing a cold thermal effect comprising applying an effective amount onto the skin or into the oral cavity of a human subject in need of or desirous of a cold thermal effect, a cooling agent of general formula (I)

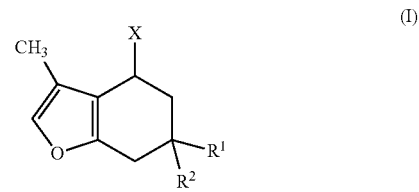

in which:
$R^1$ and $R^2$ are chosen independently of each other as a hydrogen atom or a $C_1$-$C_6$-alkyl group; and
X represents =O, -OAc, —O—$C_1$-$C_6$-alkyl, —N—OH or —OH.

2. The method comprising applying a cooling agent of a compound of general formula (I) according to claim 1, wherein $R^1$ and $R^2$ are chosen independently of each other as being a hydrogen atom or a —$CH_3$, —$C_2H_5$ or —$(CH_2)_2CH_3$ group.

3. The method comprising applying a cooling agent of a compound of general formula (I) according to claim 1, wherein $R^1$ and $R^2$ are identical and are chosen as being a hydrogen atom.

4. The method comprising applying a cooling agent of a compound of general formula (I) according to claim 1, wherein X represents =O, —OAc or —OH.

5. The method comprising applying a cooling agent of a compound of general formula (I) according to claim 4, wherein X represents =O.

6. The method comprising applying a cooling agent of a compound of general formula (I) according to claim 1, wherein the compound of general formula (I) is evodone.

7. The method comprising applying a cooling agent of a compound of general formula (I) according to claim 1, wherein the cooling agent is applied in a composition in a ratio of from 0.005% to 75% by total weight of the composition.

8. The method comprising applying a cooling agent of a compound of general formula (I) according to claim 7, wherein the ratio is from 0.01% to 25%.

9. The method comprising applying a cooling agent of a compound of general formula (I) according to claim 7, wherein the ratio is from 0.1% to 5%.

10. A method comprising applying into the oral cavity of a human subject a cooling agent of general formula (I)

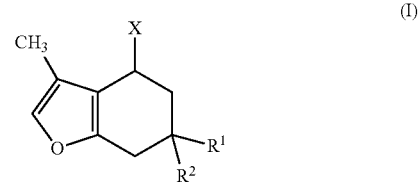

in which:
$R^1$ and $R^2$ are chosen independently of each other as a hydrogen atom or a $C_1$-$C_6$-alkyl group; and
X represents =O, —OAc, —O—$C_1$-$C_6$-alkyl, —N—OH or —OH.

* * * * *